United States Patent [19]
Fernandez-Pol

[11] Patent Number: 5,955,287
[45] Date of Patent: Sep. 21, 1999

[54] METHOD OF DETERMINING LEVEL OF BIOLOGICAL SUBSTANCES ELEVATED IN THE PRESENCE OF CANCER AND OTHER NEOPLASMS

[76] Inventor: Jose Alberto Fernandez-Pol, 437 Huners Hill Dr., Chesterfield, Mo. 63017

[21] Appl. No.: 08/928,154

[22] Filed: Sep. 12, 1997

Related U.S. Application Data

[63] Continuation-in-part of application No. 08/581,250, Dec. 29, 1995, abandoned, and a continuation-in-part of application No. 08/581,072, Dec. 29, 1995, Pat. No. 5,668,016.

[51] Int. Cl.$^6$ .................. G01N 33/53; G01N 33/531; G01N 1/18; G01N 33/567
[52] U.S. Cl. ............. 435/7.1; 435/961; 435/962; 436/177; 436/504; 436/539; 436/540; 436/804; 436/813
[58] Field of Search ................. 436/504, 539, 436/540, 543, 804, 813, 825, 179, 177, 180; 435/7.23, 7.1, 810, 961, 962, 975; 422/68.1, 72, 100–101

[56] References Cited

U.S. PATENT DOCUMENTS

| | | | |
|---|---|---|---|
| 4,658,022 | 4/1987 | Knowles | 530/402 |
| 4,999,304 | 3/1991 | Robertson . | |
| 5,243,041 | 9/1993 | Fernandez-Pol . | |
| 5,367,063 | 11/1994 | Bomalaski et al. . | |
| 5,395,753 | 3/1995 | Prakash . | |
| 5,401,767 | 3/1995 | Sindelar et al. | 514/462 |
| 5,455,159 | 10/1995 | Mulshine et al. . | |
| 5,494,803 | 2/1996 | Carbonell et al. . | |
| 5,530,100 | 6/1996 | Darling et al. . | |

OTHER PUBLICATIONS

Jose A. Fernandez–Pol, Metallopanstimulin as a Novel Tumor Marker In Sera Of Patients With Prostatic Carcinoma, Abstract 49 Journal of Tumor Maker Oncology, p. 54, 1995.
Robert K. Scopes, Protein Purification, Principels and Practice pp. 61–63.
Stansfield, Serology and Immunology, Macmillan Publishing p. 254, 1981.
Fernandez–Pol et al, Cell Growth and Differentiation vol. 5 p. 811, Aug. 1994.
Reeck et al, Cell, vol. 50 p. 667, Aug. 1987.
Lewin, Science vol. 237 p. 1570, 1987.

*Primary Examiner*—Paula Hutzell
*Assistant Examiner*—Susan Ungar
*Attorney, Agent, or Firm*—Polster, Lieder, Woodruff & Lucchesi, LC

[57] ABSTRACT

A method of performing immunoassay to detect the level of target proteins common to various malignancies including metallopanstimulin or metallopanstimulin-like materials as well as complement components, in a biologic sample is provided wherein the protein molecules in the patient sample compete with radiolabeled peptide for sites on the Anti-peptide-specific antibody. The amount of radioactivity measured is inversely proportional to the concentration of protein molecules present in the patient sample, which is determined from a standard curve. Another method includes determining the presence of a protein elevated in the serum of patients with neoplasms by the detection of the interference of binding or precipitation of a first antibody by a second antibody by the target protein.

2 Claims, 11 Drawing Sheets

| TOTAL HEALTHY SUBJECTS | 147 | 64 | 18 | 17 | 0 | 0 |
|---|---|---|---|---|---|---|
| TOTAL CANCER DISEASE | 225 | <1 | <1 | 9 | 45 | 44 |
| TOTAL NONMALIGNANT DISEASE | 260 | 56 | 19 | 21 | 3 | <1 |

| TOTAL HEALTHY SUBJECTS | 147 | 64 | 18 | 17 | 0.1 | 0.1 |
|---|---|---|---|---|---|---|
| TOTAL CANCER DISEASE | 225 | 1 | 1 | 9 | 45 | 44 |
| TOTAL NONMALIGNANT DISEASE | 260 | 56 | 19 | 21 | 3 | 1 |

ASSAY FLOW CHART

| TUBE NUMBER | TUBE IDENTIFICATION | BUFFER D/Z | DILUENT P | CALIBRATORS/ CONTROLS | PRIMARY ANTIBODY | INCUBATION | 125-I PEPTIDE N | INCUBATION | 2nd Ab/PEG PRECIPITATION | INCUBATION | CENTRI- FUGATION |
|---|---|---|---|---|---|---|---|---|---|---|---|
| 1,2 | TC | 0 | 0 | 0 | 0 | | 100 μL | | 0 | | |
| 3,4 | NSB | 50 μL | 150 μL | 0 | 0 | | | | 1.0 mL | | |
| 5,6 | MB | 50 μL | 50 μL | 0 | 100 μL | | | | | | |
| 7,8 | A. 2 ng/mL | 0 | 0 | 100 μL | | | | | | | 3,000 x g |
| 9,10 | B. 10 ng/mL | 0 | 0 | 100 μL | | 5 MIN. ROOM TEMP | VORTEX ALL TUBES | 17 HOURS 4°C | VORTEX ALL TUBES | 6 MIN. 4°C | FOR 20 MIN. 10°C |
| 11,12 | C. 50 ng/mL | 0 | 0 | 100 μL | VORTEX ALL TUBES | | | | | | |
| 13,14 | D. 200 ng/mL | 0 | 0 | 100 μL | | | | | | | |
| 15,16 | E. 500 ng/mL | 0 | 0 | 50 μL | | | | | | | |
| 17,18 | R-MPS-1 | 50 μL | 0 | ✱ | | | | | | | |
| 19,20 | LOW SERUM, CO | 0 | 0 | ✱ | | | | | | | |
| 21,22 | HIGH SERUM, CO | 0 | 0 | ✱ | | | | | | | |
| 23,24 | PATIENT 1 | 0 | 0 | ✱ | | | | | | | |
| 25,26 | PATIENT 2 | 0 | 0 | ✱ | | | | | | | |
| 27,28 | PATIENT n | 0 | 0 | ✱ | | | | | | | |

TC: TOTAL COUNTS; NSB: NON-SPECIFIC BINDING; MB: MAXIMUM BINDING; 2ndAb/PEG: SECONDARY ANTI-RABBIT ANTIBODY/PEG SOLUTION
✱ USE 50 μL OF ACTIVATED SUPERNATANT
CO: CONTROL PATIENT SERUM

FIG. 13

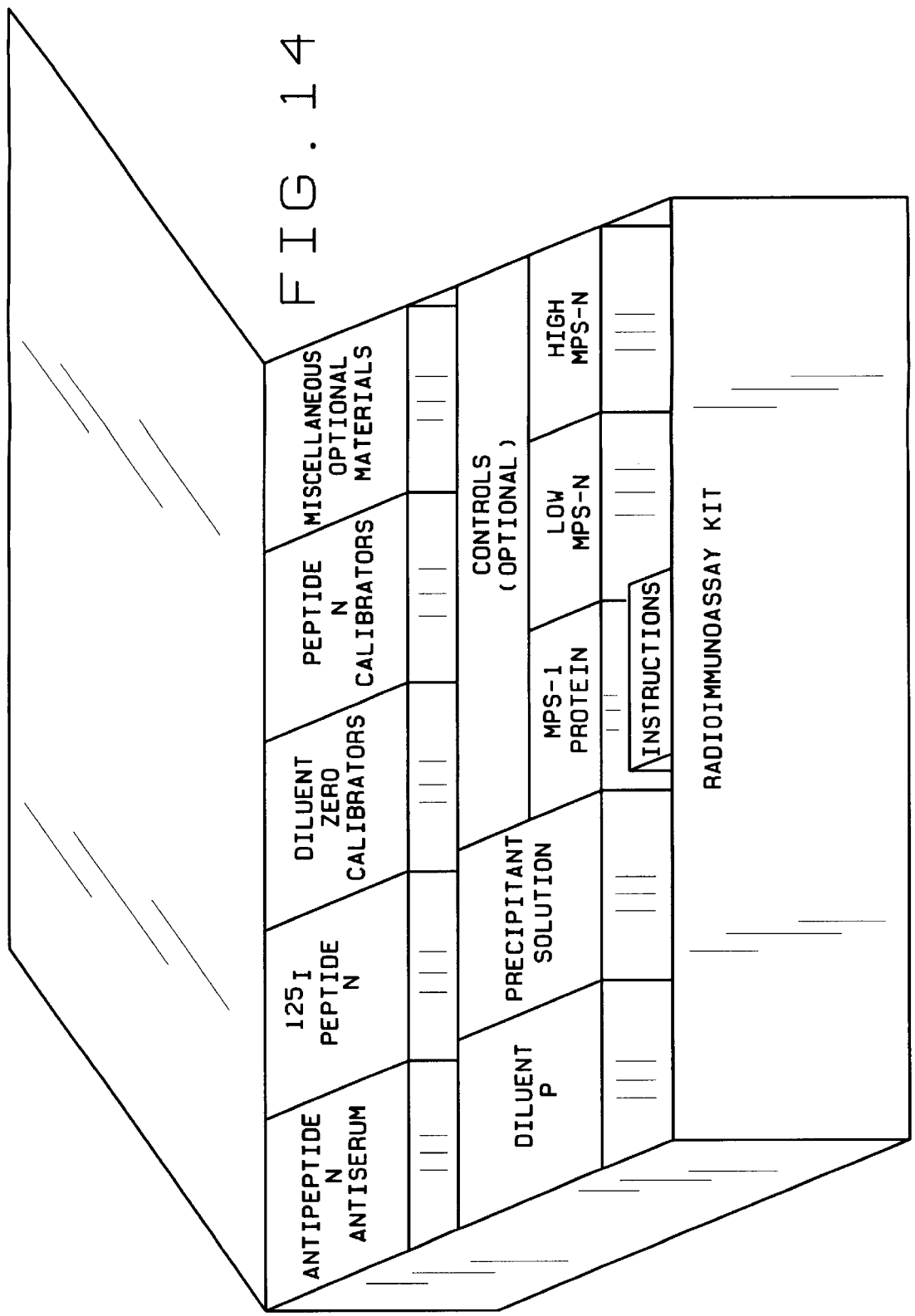

WESTERN BLOT ANALYSIS OF HEATED HUMAN SERUM FROM A PATIENT WITH METASTATIC PROSTATE CARCINOMA USING ANTI-MPS-N ANTIBODIES

METHOD OF DETERMINING LEVEL OF BIOLOGICAL SUBSTANCES ELEVATED IN THE PRESENCE OF CANCER AND OTHER NEOPLASMS

CROSS-REFERENCE TO RELATED APPLICATIONS

This application is a continuation-in-part of application Ser. No. 08/581,250, filed Dec. 29, 1995, now abandoned, and a continuation-in-part of application Ser. No. 08/581,072, filed Dec. 29, 1995, now U.S. Pat. No. 5,668,016.

BACKGROUND OF THE INVENTION

This invention relates generally to medical diagnostics and, more particularly to a novel and simplified method of detecting neoplasias including benign and malignant tumors by an unconventional assay measurement of proteins common to various forms of cancers, such proteins include MPS-1, MPS-1-like proteins, MPS-N and MPS-N-like materials, complement and other proteins in human serum, as well as to various apparatus for performing the method.

The test of the present invention is based on the discovery of a novel gene, denoted METALLOPANSTIMULIN (MPS), which encodes a protein associated with many human cancers. Although the original invention was based upon the discovery of the novel MPS gene, the inventor subsequently developed methods for determining the presence of proteins both related to and unrelated to MPS that are elevated in cancers and other proliferative diseases, and which are part of the subject matter of this application.

The novel DNA sequence which encodes the METALLOPANSTIMULIN is described in detail in U.S. Pat. No. Re. 35,585, which is hereby incorporated by reference. METALLOPANSTIMULIN is "zinc finger" protein of sub-unit molecular weight approximately 10,000-Dalton is designated as "METALLOPANSTIMULIN" (MPS) since:

1) it forms a complex with metal ions such as zinc (Greek: metallo);
2) it has been detected in many different cell types (Greek: pan=all); and
3) it is associated with rapid cell proliferation (Latin: stimulin). MPS is a multifunctional protein with at least three main functions:

1) it has a nuclear localization signal and it can bind specific DNA sequences probably acting as a modulator of transcription;
2) the MPS protein stimulates cell growth;
3) it also is associated with ribosomes; and
4) the MPS protein is secreted from the cells into extra-cellular fluids.

MPS-N is the metallopanstimulin-N-terminal sequence up to the first cysteine residue, described in the patent. MPS-N like proteins are proteins having at least 35% sequence homology with the N-terminal portion of MPS-1. MPS-1 is the authentic human MPS, first cloned from a human breast cancer cell line and subcloned in baculovirus, as described in U.S. Pat. No. Re. 35,585, which, as stated above, is incorporated herein by reference. MPS-1 is used as the standard of reference for any studies involving MPS. MPS-like proteins have at least 35% amino acid sequence homology with MPS-1.

Numerous experiments with human tissue culture cells and human pathological tissue specimens demonstrated that the MPS-1 mRNA and its encoded protein are expressed in normal cells to a much lesser degree than in premalignant or malignant tumor cells, and they are present at very low levels in senescent cells compared to young healthy cells. The inventor also has discovered that other MPS-like proteins, that is, proteins having at least 35% amino acid sequence homology with MPS proteins also are expressed in higher levels in premalignant and malignant cells. Further, additional proteins, for example certain types of complement and segments of complement also are found to be elevated in premalignant and malignant cells.

It is believed that cancer detected early is more susceptible to therapy than cancer detected late. Early detection of cancer is important in two general situations:

1) detection of primary disease in asymptomatic, previously undiagnosed individuals; and
2) detection of cancer recurrence in previously diagnosed and treated patients. The ability to identify cancer at an early stage may be useful to administer an effective therapy.

A reliable test for detecting malignant cell proliferation, when the tumor is confined and effective treatment can be provided, would be of great value for the physician. At present, the majority of cancers have advanced beyond the organ of origin at the time of diagnosis.

The measurement of MPS-N and MPS-N-like materials and complement in human serum is of primary interest in the detection of active malignant proliferative processes. For example, the results of clinical correlation studies to date indicate that MPS-N is frequently (>90% of the cases) elevated (>10 ng/ml) in a large number of active common malignancies, such as prostate, colorectal, lung and other cancers. Thus, MPS-N testing has significant value in detecting undiagnosed malignant cell proliferation and/or active oncogenic processes. The monitoring of patients with diagnosed malignancies in which changes in concentrations of MPS-N are observed is also of significant clinical value. The above clinical studies indicated that a heretofore unidentified protein, suspected to be an MPS-like protein, also was elevated in common malignancies. Through further research the inventor has determined that the heretofore unidentified protein is a segment of a form of complement which is elevated linearly in the sera of patients with cancer.

An extensive clinical study including 632 individuals separated in healthy subjects, active cancerous diseases, non-malignant diseases, and premalignant diseases has provided important information about the use of MPS-N in the detection of various types of cancer. The data from the clinical study is provided below in Table 1 and also illustrated graphically in FIGS. 1A and 1B.

In general, the MPS-N test was found to be useful in:

1) Detection of primary disease in previously undiagnosed individuals; and
2) Detection of cancer recurrence in previously diagnosed and treated patients.

TABLE 1

DISTRIBUTION OF MPS VALUES
NUMBER OF PATIENTS: 632

|  | Number | <7.0 | 7.0–10 | 10.01–20 | 20.01–50 | >50.01 |
|---|---|---|---|---|---|---|
| HEALTHY SUBJECTS | | | | | | |
| Women (19–64 years) | 20 | 70 | 20 | 10 | 0 | 0 |
| Men (21–55 years) | 20 | 65 | 10 | 25 | 0 | 0 |
| Men (50–88 years) | 107 | 62 | 20 | 18 | 0 | 0 |
| TOTAL | 147 | 64 | 18 | 17 | 0 | 0 |
| CANCEROUS DISEASES, ACTIVE | | | | | | |
| Genitourinary Tract | | | | | | |
| Prostate | 126 | 1 | <1 | 11 | 48 | 38 |
| Bladder | 6 | 0 | 0 | 0 | 33 | 66 |
| Testicular | 1 | 0 | 0 | 0 | 0 | 100 |
| Gastrointestinal Tract | | | | | | |
| Esophageal | 3 | 0 | 0 | 33 | 66 | 0 |
| Pancreatic | 1 | 0 | 0 | 0 | 0 | 100 |
| Hepatoma | 2 | 0 | 0 | 0 | 50 | 50 |
| Colorectal | 27 | 0 | 0 | 7 | 44 | 48 |
| Lung Cancer | | | | | | |
| Epithelial malignancies | 27 | 0 | 0 | 11 | 26 | 63 |
| Head and Neck Region | | | | | | |
| Epithelial malignacies | 6 | 0 | 0 | 0 | 66 | 33 |
| Central Nervous System | | | | | | |
| Primary Necplasms | 1 | 0 | 0 | 0 | 0 | 100 |
| Neuroendocrine origin | 6 | 0 | 0 | 17 | 17 | 66 |
| Leukemia and lymphoma | 7 | 0 | 0 | 0 | 43 | 57 |
| Other Malignancies | 12 | 0 | 0 | 0 | 58 | 42 |
| TOTAL | 225 | <1 | <1 | 9 | 45 | 44 |
| NONMALIGNANT DISEASES | | | | | | |
| Benign Prostatic Hypertrophy | 37 | 30 | 16 | 38 | 13 | 3 |
| Hepatitis, B,C. | 18 | 83 | 5 | 11 | 0 | 0 |
| Liver cirrhosis | 4 | 100 | 0 | 0 | 0 | 0 |
| Other | 201 | 58 | 21 | 20 | 1 | 0 |
| TOTAL | 260 | 56 | 19 | 21 | 3 | <1 |
| Premalignant disease | | | | | | |
| Colorectal Polyps | 4 | 0 | 0 | 0 | 75 | 25 |

*Other Malignancies: include cancer of unknown origins, squamous cell carcinomas, etc.

As illustrated, the quality criteria of the MPS-N test as a tumor marker, characterized by its diagnostic specificity (percentage of healthy individuals [82%] or benign diseases [75%] with a true negative test result); its sensitivity (percentage of true positive test results if cancer disease is present [98%]); and the cutoff value (concentration of MPS-N that differentiates healthy subjects or patients with benign disorders from those with premalignant or malignant disorders) clearly indicates that the MPS-N test has high specificity (>75%) and sensitivity (>98%) as a tumor marker.

The quantity of the MPS-N marker detectable is proportional to the extent of active malignancy as demonstrated by the following example of patients with prostatic carcinoma (PC). In patients not having PC, the MPS-N levels were lower than 10 ng/ml. In untreated patients having PC stages T1/T2, the MPS-N level range was 10–30 ng/ml; in stages T3/T4 the MPS-N level range was 30–50 ng/ml; and in stage M1b (distant metastasis to bone) the MPS-N levels were extremely high (100–500 ng/ml). In M1b patients that did not respond to therapy, the MPS-N levels remained very high (200 ng/ml). In M1b patients that went into remission after treatment, the MPS-N levels were greatly reduced. Thus, the increase in serum MPS-N correlated with the stage of the disease and response to therapy. The foregoing data originally was published in Fernandez-Pol, J. A, Klos, D. J., and Hamilton, P. D., *The Evaluation of Metallopanstimulin As A Novel Tumor Marker in Sera of Patients With Prostatic Carcinoma*, European J. of Nuclear Medicine, Supp. Vol. 21, No. 10; 94 (Abs) (1994); Fernandez-Pol, J. A, Klos, D. J., and Hamilton, P. D., *Metallopanstimulin As A Novel Tumor Marker In Sera Of Patients With Prostatic Carcinoma*, J. Tumor Marker Oncology, June 1995, (Abs. No. A49) p 54, which are hereby incorporated by reference.

Therefore, detection of primary prostate cancer in previously undiagnosed individuals can be accomplished by the serial measurement of MPS-N, provided that other types of cancers producing MPS-N materials are excluded. When employed for the management of prostate cancer patients, serial measurements of MPS-N is useful in detecting residual tumor and recurrent cancer after radical prostatectomy. Moreover, MPS-N is useful for assessing response of prostate cancer to therapy by prostatectomy, radiotherapy, and hormone therapy. Thus, serial measurements of MPS-N concentrations can be an important indicator in monitoring patients with prostate cancer and in determining the actual effectiveness of surgery and/or other treatments.

The MPS-N test also has significant importance in the detection of numerous types of undiagnosed common malignancies. As shown in Table 1, increased MPS-N levels have been detected with high frequency (>90% of the cases) in numerous types of common cancers such as prostate, colorectal, lung, neuroendocrine, leukemias, etc. Moreover, in patients having these types of cancers, MPS-N testing can have important value in monitoring metastatic or persistently active cancer, following chemotherapy, surgery, or radiotherapy. A persistent elevation in circulating MPS-N levels following treatment or increase in an otherwise lower level is indicative of recurrent or residual cancer and poor therapeutic response. A declining MPS-N value is generally indicative of a good response to treatment and a favorable prognosis.

Serum MPS-N can also be elevated in active nonmalignant tumorigenic processes and premalignant proliferative conditions such as benign prostatic hypertrophy and colorectal polyps, respectively (Table 1). Inflammatory conditions of the prostate, liver, intestine and colon are negative for MPS-N (Table 1, section on "Hepatitis, Cirrhosis, Other").

It has been shown that the MPS-1 DNA sequence and the protein can be used in diagnostic methods such as detection of malignant cells associated with several types of tumors. The development of a sensitive and specific radioimmunoassay (RIA) for MPS-N, using synthetic peptide technology, would make it possible to detect the very low concentrations of MPS-N and MPS-N-like materials in human blood and other body fluids. Thus, the MPS-N RIA provides a method for determining the presence of certain types of abnormal proliferative conditions and/or active oncogenic processes in patients as described below.

Although it was suggested in the '041 patent that radioimmunoassay techniques possibly could be employed to detect MPS levels, a simple and cost effective method for performing radioimmunoassay on a large number of individual samples, for example in a routine clinical screening, was not taught or disclosed. More importantly, no prior art reference suggested or taught a method of activating the MPS-like proteins in the serum sample which would allow detection of the MPS-N antigen. Furthermore, no reference known to the inventor teaches or suggests a low-cost kit containing materials that can easily and economically be used by a diagnostician to perform radioimmunoassay for MPS-N like materials.

BRIEF SUMMARY OF THE INVENTION

It is, therefore, among the principal objects of the present invention to provide a simplified method of performing radioimmunoassay to detect the levels of proteins common to various forms of cancers.

Another object of the invention is to provide such a method that includes a novel procedure for activating metallopanstimulin or metallopanstimulin-like proteins in a biologic fluid which, in turn, allows the detection of an MPS-N antigen.

It is another object of the present invention to provide the materials needed to perform the method of performing radioimmunoassay in a kit form.

It is yet another object of the present invention to provide a simplified method of performing radioimmunoassay to detect the levels of metallopanstimulin or metallopanstimulin-like materials in a biologic fluid, for example sera that allows cost-effective, large scale application of the method to detect carcinoma in a large scale patient population.

Still another object of the present invention is to provide such and method of performing radioimmunoassay and a kit for performing the method that is economically produced, appropriately packaged, easy to use, reliable and accurate, and well-suited for its intended purposes.

It is another object of the invention to provide a method of performing radioimmunoassay to detect metallopanstimulin or metallopanstimulin-like materials in a biologic fluid.

It is another principal object of the invention to provide a method of performing an unconventional assay to determine the level of proteins common to various forms of cancers.

Another object of the present invention is to provide such a unconventional method of performing an assay where proteins common to various forms of cancers interfere with the binding and/or precipitation of a first antibody by a second antibody, thereby exhibiting the presence of such proteins.

Yet another object of the present invention is to provide such an assay that can determine the level of complement or segments of complement that interfere with the precipitation of a first antibody by a second antibody.

Another object of the invention is to provide an apparatus for the quick and reliable determination of the presence of a substance in the serum of a patient associated with various forms of cancer.

In accordance with the invention, a method of performing radioimmunoassay to detect the level of a protein common to a variety of cancers, for example the protein metallopanstimulin or metallopanstimulin-like materials in a biologic fluid, for example sera is provided wherein MPS-N and MPS-N-like molecules in the patient sample compete with a radioactive peptide, for example $^{125}$I-peptide-N for sites on the Anti-peptide-N-specific antibody. The antibody is directed towards a unique site on the MPS-1 molecule. After incubation for a set time, separation of bound from free is achieved by a PEG-double-antibody procedure. The tube is then counted in an appropriate device, for example a gamma counter. The amount of radioactivity measured is inversely proportional to the concentration of MPS-N and MPS-N-like molecules present in the patient sample, which is determined from a standard curve. The standard curve is based on the simultaneous testing of the peptide-N standards from 0 to 500 ng/ml. The method includes novel steps for activating the MPS-like proteins in the patient sample which allows for detection of the MPS-N antigen.

BRIEF DESCRIPTION OF THE SEVERAL VIEWS OF THE DRAWINGS

FIG. 13 is a flow chart illustrating the radioimmunoassay method of the present invention;

FIG. 14 is a diagram illustrating the kit for performing the radioimmunoassay of the present invention;

DETAILED DESCRIPTION OF THE INVENTION

One embodiment of the procedures of the present invention includes the detection of elevated levels of MPS proteins by the addition of a first antibody with affinity for the MPS proteins to an activated or prepared serum sample. A second, labeled antibody is added which has an affinity for the first antibody. The addition of the second antibody causes a precipitation of the protein antibody complex. The amount of labeled complex precipitated then can be measured to give a determination of the amount of the MPS proteins in the sample.

In general one radioimmunoassay of the present invention can be performed with the reagents and in the manner as will be described in detail below. In general, MPS-N and MPS-N-like molecules in the patient sample compete with a radioactive peptide, for example $^{125}$I-peptide-N for sites on the Anti-peptide-N-specific antibody. The antibody is directed towards a unique site on the MPS-1 molecule. After incubation for a set time, separation of bound from free is achieved by a PEG-double-antibody procedure. The tube is then counted in an appropriate device, for example a gamma counter. The amount of radioactivity measured is inversely proportional to the concentration of MPS-N and MPS-N-like molecules present in the patient sample, which is determined from a standard curve. The standard curve is based on the simultaneous testing of the peptide-N standards from 0 to 500 ng/ml. The method includes novel steps for activating the MPS-like proteins in the patient sample which allows for detection of the MPS-N antigen. The radioimmunoassay involves a total incubation time of 17 h at 4° C. A calibration curve and 20 patient samples is prepared in less than an hour. Broadly speaking, separation is attained by a precipitating solution consisting of a second antibody against rabbit primary antibody and a solution of PEG. The precipitation reaction is completed in a set time at 4° C. in an ice bath, which has been shown to yield reproducible results. The precipitate is solid, easily perceptible and non-specific binding is low. The PEG solution is supplied as ready to use.

Figure 1A:
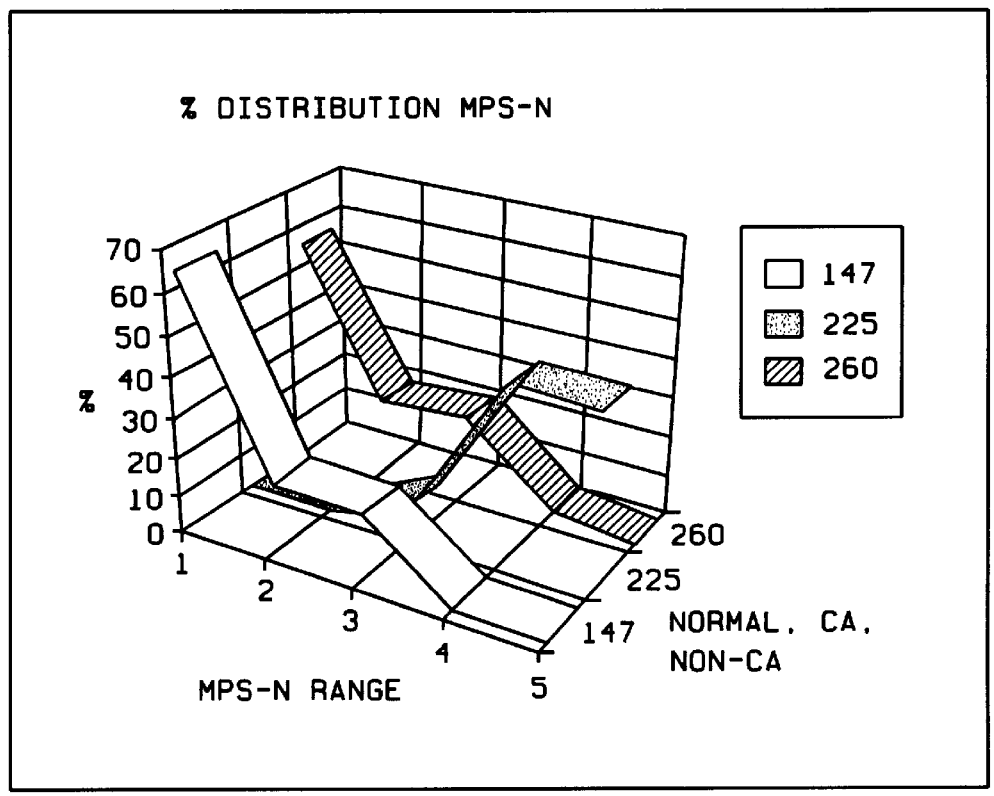
FIG. 1A is a graph illustrating the percentage distribution of MPS-N.
Figure 1B:
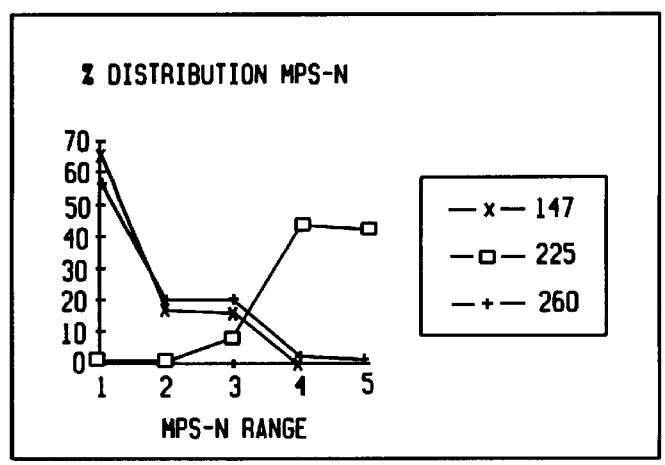
FIG. 1B is another graph illustrating the percentage distribution of MPS-N.
Figure 2A:
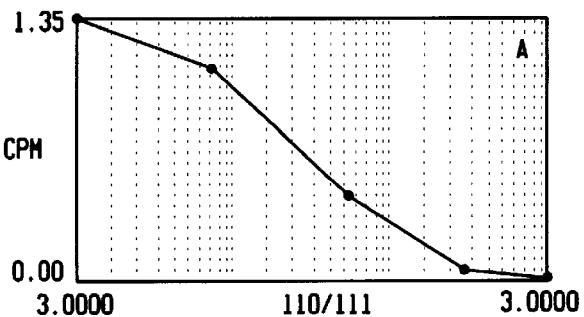
FIG. 2A is a graph illustrating the results of MPS-N test assay in semi-log point-to-point format.
Figure 2B:
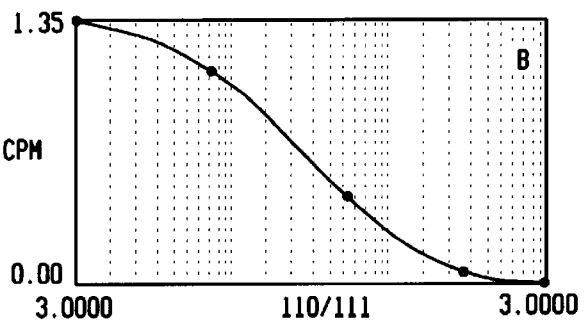
FIG. 2B is a graph illustrating the results of MPS-N test assay in 4-parameter logistic format.
Figure 2C:
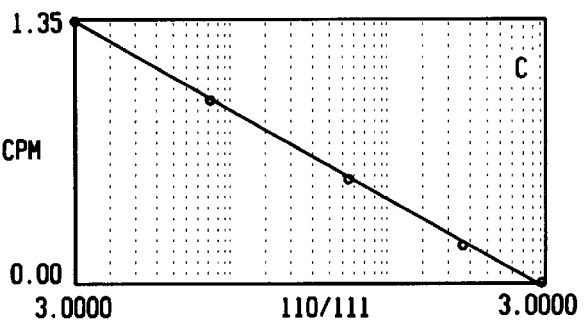
FIG. 2C is a graph illustrating the results of MPS-N test assay in Logit/Log format.

Methods for standard data analysis and quality control are provided. The assay is optimized for linearity in a Semi-Log point-to-point, 4-parameter logistic, or Logit/Log representation in the range of the calibrators (FIGS. 2A, 2B, and 2C, respectively).

The kit of the present invention includes calibrators with specific values ranging from 2 to 500 ng/ml. The calibrators are protein-based to eliminate serum protein matrix effects.

The radioactively labeled peptide-N has a high specific activity. The initial total counts are 30,000 to 40,000 cpm. The maximum binding is approximately 40–50%, which increases sensitivity and is adequate for precision.

Figure 3:
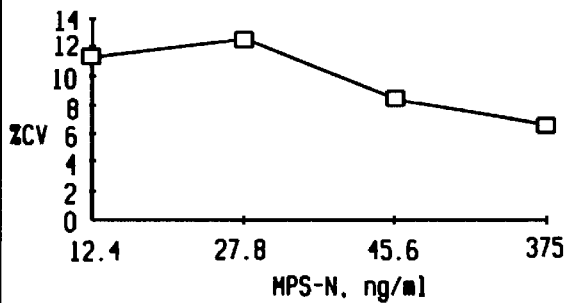
FIG. 3 is a graph illustrating intraassay precision.

Intraassay coefficient of variation is better than 13%, as shown below in Table 2 and in FIG. 3.

TABLE 2

| Intraassay Precision (Within Run) | | | | |
|---|---|---|---|---|
| Serum Sample | 1 | 2 | 3 | 4 |
| No of Replicates | 20 | 20 | 20 | 20 |
| Mean (ng/mL) | 12.4 | 27.8 | 45.6 | 375 |
| SD | 1.4 | 3.5 | 3.9 | 25.6 |
| CV (%) | 11.3 | 12.6 | 8.5 | 6.8 |

Figure 4:
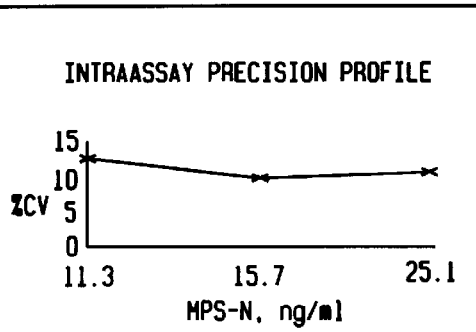
FIG. 4 is a graph illustrating interassay precision.

Interassay coefficient of variation is approximately 12%, as shown below in Table 3 and also in FIG. 4.

TABLE 3

| | Interassay (Between Run) | | |
|---|---|---|---|
| Serum Sample | 1 | 2 | 3 |
| No of Assays | 10 | 10 | 10 |
| Mean (ng/mL) | 11.3 | 15.7 | 25.1 |
| SD | 1.4 | 1.5 | 2.7 |
| CV | 12.4 | 9.6 | 10.8 |

The assay can detect as little as 2 ng/ml. No "end-of-run" assay effect has been observed in assays involving over 60 tubes, as shown in Table 5, discussed hereinafter. However, PEG precipitation in sets of 60 tubes are recommended, to minimize the effect of different incubation times with PEG.

The antiserum is highly specific for the N-terminal region of MPS. Peptide-N, a synthetic peptide corresponding to the N-terminal portion of MPS, amino acid residue 1-17, completely neutralizes the binding of Anti-peptide-N antibodies to human recombinant MPS-1 protein. Furthermore, a search of the sequence database Gene Bank$^R$ indicates that the peptide-N has less than 12% sequence homology with all the protein sequences stored in this data bank. The antibody against the N-terminal region does not react with MPS peptides corresponding to the mid-region ("Zinc Finger") or C-terminal regions of human recombinant MPS-1 protein.

Experiments show that the assay is accurate over a broad range of values (2–100 ng/ml). Its accuracy has been verified by recovery and dilution studies with peptide-N, human recombinant MPS-1, and human patient sera containing MPS-N. Based on a study of 147 individuals of ages from 19 to 88 years, the RIA for MPS-N has a reference range for adults of nondetectable to 10 ng/ml (82% specificity; Table 1, above).

The Kit of the Present Invention

To perform the radioimmunoassay method of the present invention directed to detecting MPS and MPS-N like proteins following a procedure that will be described in detail below, the essential materials can be provided in a kit form as illustrated in FIG. 14, and comprise as follows:

One vial(7 ml) Anti-peptide N Antiserum

The anti-peptide N antiserum contains polyclonal rabbit IgG anti-peptide N antibody, containing 0.2% NaN$_3$ (sodium azide) as a preservative. Store refrigerated: stable at 2–8° C. for at least 45 days.

One bottle (7 ml) of radiolabeled peptide, for example, $^{125}$I-labeled peptide-N ($^{125}$I-peptide N)

A radiolabeled peptide N is used in the procedure. In the preferred embodiment, $^{125}$I-labeled peptide N is used. However, any appropriate radio label may be employed.

One vial of iodinated peptide N in a protein matrix, albumin, is provided containing less than 2 uCi/vial and 0.2% sodium azide as a preservative. The peptide should be refrigerated and is stable at 2–8° C. for at least 45 days or until expiration date indicated on the label.

One bottle (10 ml) Diluent/Zero Calibrator (Buffer D/Z)

A protein matrix solution is provided containing no detectable concentration of MPS-N (0 ng MPS-N/ml) and 0.2% sodium azide as a preservative. The BufferD/Z is prepared as follows: Weigh out 8 g of bovine serum albumin and 200 mg sodium azide and dissolve in approximately 90 mL of Diluent P, which will be described below. After the albumin and sodium azide are in solution, bring up to 100 mL with Diluent P in a 100 mL volumetric flask. The buffer should be refrigerated and is stable up to one month.

Peptide N calibrators (A to E)

Five bottles (1 ml each) of peptide N calibrators, identified as A,B,C,D, and E, in a protein matrix and 0.2% sodium azide as a preservative are provided. Each of these bottles, respectively, yield final concentrations in the assay tubes of 2, 10, 50, 200, and 500 ng of peptide N per milliliter. The calibrators should be refrigerated and are stable at 2–8° C. for at least 45 days.

One bottle (20 ml) Diluent P

Diluent P, as provided, is a specially prepared phosphate buffer saline solution which can be prepared as follows: Place 20 mL of 10× Dulbecco's Phosphate-Buffered Saline (DPBS) with NO calcium and magnesium (Gibco Catalog No.14200-026) in a 200 ml volumetric flask. Bring to 200 mL with deionized water. The pH should be 7.3±0.1. Filter sterilize. The diluent should be refrigerated and is stable up to 45 days.

Precipitating solution GAR/PEG (One bottle: 100 ml)

One bottle of goat anti-rabbit gamma globulin (GAR) and polyethylene glycol (PEG) in saline is provided. The precipitating solution is supplied in liquid form, ready to use. The solution should be refrigerated and is stable at 2–8° C. for at least 45 days. Because a fine precipitate may form after storage at 2–8° C., the PEG solution should be thoroughly mixed before use. The precipitating solution should be used immediately after opening and unused portion discarded.

Occasionally one may encounter high counts in all patient samples which lead to uniformly low results. The cause is contamination or deterioration of the PEG precipitating solution. Therefore, the PEG precipitating solution should be used only once after opening.

Storage and Stability

The kit should be stored at 2–8° C. and in its original container. The kit is stable until the expiration a date printed on the box label. All reagents must be brought to room temperature (18° C. to 25° C.) prior to use. After use, all reagents should be stored at 2° C. to 8° C. Repeated freezing and thawing of the materials should be avoided.

If precipitates or turbidity in a reagent solution is noted, this may be suspected as reagent instability or deterioration.

Controls

The control materials may be provided as optional materials in the kit or may be provided separately. MPS-N controls are prepared with human recombinant MPS-1 protein and human sera containing low and high concentrations of MPS-N protein as follows.

1. Recombinant human MPS-1 protein (One vial; lyophilized MPS-1 protein)

Lyophilized baculovirus produced human recombinant MPS-1 protein at 25–50 ng/ml and 0.2% sodium azide as a preservative is one control. Each vial is reconstituted with 0.5 ml distilled or deionized water. The reconstituted product is divided into aliquots and frozen at −20° C. to avoid repeated freezing and thawing when performing additional assays. It is stable when stored at −20° C. up to one year after reconstitution.

2. Low MPS-N control (One vial; lyophilized human plasma)

The Low MPS-N control contains approximately 2 to 7 ng of MPS-N per ml in a protein matrix and 0.2% sodium azide as a preservative. Each vial is reconstituted with 0.5 ml distilled or deionized water divided into aliquots and frozen at −20° C. to avoid repeated freezing and thawing when performing additional assays. The control is stable when stored at −20° C. up to two months after reconstitution.

3. High MPS-N control (One vial; lyophilized human plasma)

High MPS-N control contains approximately 30 to 50 ng of MPS-N per ml in a protein matrix and 0.2% sodium azide as a preservative. Each vial is reconstituted with 0.5 ml distilled or deionized water divided into aliquots and frozen at −20° C. to avoid repeated freezing and thawing when performing additional assays. The control is stable when stored at −20° C. up to two months after reconstitution. The following list of materials are required but not necessarily provided in the kit of the present invention:

Gamma counter
Centrifuge: refrigerated and capable of at least 14,500×g.
Test tube rack
Repeating pipettor: 2 ml (±1%)
Disposable tip precision pipettor: 50 uL (±1%)
Repeating precision pipettors: 200 uL (±1%)
Boiling water bath
Distilled or deionized water
Volumetric pipettes: 2.0, 5.0 and 10 ml.
Plain 12×75 mm polypropylene tubes, round bottom.
Micropipets: 100 uL and 10 ml. For the 100 uL additions a reliable repeating dispenser is recommended. A dispenser accurate to within 0.05 ml is recommended for the 1.0 ml addition of the PEG precipitating solution.
Vortex mixer.
Paper towels.
A bi-level (low and high) human serum-based immunoassay controls, containing MPS-N.

The Method of Performing Radioimmunoassay

Preparation of Reagents

The reagents are prepared as follows: Bring all reagents and specimens to room temperature (18° C.–25° C.) prior to use. Thoroughly mix the reagents before each use by gentle agitation. Avoid cross-contamination by using a clean pipette tip for each vial and specimen. Reconstitute the lyophilized reagents with the amount specified below using distilled or deionized water. After reconstitution, allow the vials to stand at room temperature (18–25° C.) several minutes. Mix thoroughly by gentle inversion.

Specimen Collection and Preparation

The specimen is collected and prepared as follows: No special patient preparation is necessary. Collect 5 ml of blood by venipuncture into plain tube (red top; marble top). Allow the blood to clot and separate the serum from the cells by centrifugation. Do not use heparinized or EDTA tubes. Avoid hemolysis. A biologic fluid sample is required. For example, serum is required for the RIA of MPS-N. Plasma samples should not be used. The biologic fluid sample, for example the serum specimen can be stored in a refrigerator at 2° C. to 8° C. for up to 24 h after collection. Specimens that can not be analyzed within 24 h should be frozen at −20° C. or colder. Mix thoroughly after thawing to assure consistency in the results. The procedure requires 50 uL of serum per assay tube. Unless assay immediately, samples should be aliquotted and frozen without delay after collection. Freeze and thaw only once. The samples can be stored at −20° C. for up to 3 months. Before assay, thaw the samples at room temperature and mix by inversion. Do not thaw frozen specimens by heating them in a water bath. As with numerous other assays hemolysis and lipemia may interfere with the assay. Specimens showing particulate materials, turbidity, erythrocytes, etc, should be clarified by centrifugation before testing.

Preparation of the Sample

The inventor has determined that a unique and heretofore unknown method of activating the proteins in the serum sample allows the method of the present invention to work. The novel method is disclosed in co-pending application Ser. No. 08/581,072, now U.S. Pat. No. 5,668,016, which is hereby incorporated by reference. The method of activating or preparing the proteins for testing includes heating the serum samples in a diluent devoid of calcium and magnesium so as to partially denature the unwanted proteins and liberate the target MPS and MPS-N like proteins without activating the calcium- and magnesium-dependent proteases that can destroy the target proteins. The following procedures describe the novel procedure for activating the target proteins in the sample.

The serum samples are activated to partially denature the protein and liberate the target proteins as follows:

Add 200 µl of serum to 400 µl of Diluent P, mix, and put in a boiling water bath for approximately 3 to 5 minutes, preferably 3 minutes. Samples are allowed to cool at room temperature for three minutes, and centrifuged at 14,000×g at 2–4° C. for 20 minutes. Supernatants are carefully removed and subsequently vortexed well to ensure homogeneity. Then, 50 µl aliquots of the supernatant are assayed in duplicated. To avoid mixing do not pipette close to the interface.

Radioimmunoassay Procedure

Bring all kit components to room temperature and mix well before use. All Calibrators, Controls, and Patient Specimens should be tested in duplicate simultaneously. Attachment to this protocol and accuracy in all pipetting steps are fundamental to ensure excellent results. The assay procedure is as follows:

Assay for MPS-N

The assay for MPS-N is performed according to the flow chart as illustrated in FIG. 13.

1. Label 16 tubes in duplicate to include: Total Counts (TC): nonspecific binding (NSB), Maximum Binding (MB), and calibrators A through E. Label additional tubes in duplicate for controls (Recombinant MPS generated by baculovirus in accordance with the methods described in U. U. Pat. No. Re 35,585, low and high sera), and patient samples.

2. Pipette 50 uL of buffer D/Z and 150 uL of Diluent P into the NSB tubes.

3. Pipette 50 uL of buffer D/Z and 50 uL of Diluent P into the MB tubes.

4. Pipette 100 uL of calibrators (A–E) into tubes A through E.

5. Pipette 50 uL of buffer D/Z and 50 uL of controls or serum samples to the respective tubes.

6. Pipette 100 uL of Rabbit Anti-Peptide N antibodies to all tubes, except the TC and NSB tubes. Incubate 5 min at room temperature.

7. Pipette 100 uL of $^{125}$I-Peptide N into all tubes. Vortex.

8. Incubate overnight (17 h) at 4° C.

9. After overnight incubation, all samples are placed in an ice water bath.

Rapidly add 1.0 mL of cold, well mixed PEG precipitating solution to all tubes and vortex immediately. Allow 6 min for complete precipitation. Note: add PEG to sets of tubes with no more than 60 tubes per set and proceed immediately to the next step (centrifugation). Otherwise, the precipitating times are different, and this may cause in certain instances different amounts of precipitate.

10. Centrifuge 20 min at 3,000×g at 10° C.

11. Without delay, decant the supernatant, blot the residual droplet which remains in each tube by using an absorbent paper, retaining the precipitate for counting.

12. Count each tube for 1 min in a gamma counter and record the counts per minute.

13. Calculate the results as described below in the description of sample data, calculation, and standard curve.

It will be appreciated that non-specific binding was measured in the absence of anti-peptide N antibodies. All results are calculated considering the dilutions made to original serum sample.

Special Consideration

1. When a value greater than 100 ng/ml is detected in a specimen, the specimen should be diluted with buffer D/Z and assayed again. The dilution factor should be incorporated into the calculation of results. The dilutions indicated for samples measuring greater than 100 ng/ml MPS-N are 1:1 and 1:10. The diluted sample should read within the range of the standard curve and should read greater than 2 ng/ml.

EXAMPLE

A 10-fold dilution is prepared by adding 50 uL of patient sample to 450 uL of Diluent P. The sample is mixed by vortexing. 50 uL of diluted sample is added to 50 uL of Buffer D/Z before assaying. To determine the concentration of MPS-N in the specimen, multiply the concentration of the diluted sample (read by extrapolating in the standard curve) by the dilution factor. In this case, the dilution factor is (10×3)=30.

2. Disposable pipette tips should be used. The pipette tip should be change after each sample is pipetted to prevent contamination of reagents or samples.

3. To ensure consistency in the precipitation step, the size of the assay run should be limited to 62 samples per set, which is the number that can be pipetted in 7 min.

4. A repeating pipettor should be used for addition of the PEG solution.

Sample Data, Calculations, and Standards Curve

The data shown in FIGS. 2A–2C and Table 4, below, were obtained following the method of the present invention. They illustrate the expected results of the procedure. Because the calibrator values are lot-specific, the results shown in FIGS. 2A–2C and Table 4 should not be used to calculate results from another assay. The MPS-N assay results can be calculated either manually or by using computer programs.

TABLE 4

EXAMPLE OF DATA

| Tube | Description | Duplicate CPM | Average CPM | MPS ng/mL |
|------|-------------|---------------|-------------|-----------|
| 1 | TC | 25415 | | |
| 2 | | 26213 | 25814 | |
| 3 | NSB | 91.3 | | |
| 4 | | 90 | 90.5 | |
| 5 | 0 ng/mL Calibrator | 14830 | | |
| 6 | (MB) | 14584 | 14707 | |
| 7 | 2 ng/mL Calibrator A | 14083 | | |
| 8 | | 13947 | 14015 | |
| 9 | 10 ng/mL Calibrator B | 11818 | | |
| 10 | | 11595 | 11607 | |
| 11 | 50 ng/mL Calibrator C | 6195 | | |
| 12 | | 6286 | 6241 | |
| 13 | 200 ng/mL Calibrator D | 1689 | | |
| 14 | | 1661 | 1675 | |
| 15 | 500 ng/mL Calibrator E | 785 | | |
| 16 | | 775 | 780 | |
| 17 | R-MPS | 7471 | | |
| 18 | | 7238 | 7355 | 36 |
| 19 | Low Control Serum | 13775 | | |
| 20 | | 13674 | 13725 | 2.45 × 3 = 7.4 |
| 21 | High Control Serum | 8181 | | |
| 22 | | 8477 | 8329 | 27 × 3 = 81 |
| 23 | Patient Specimen A | 3294 | | |
| 24 | | 3253 | 3274 | 123 × 3 = 369 |
| 25 | Patient Specimen B | 11679 | | |
| 26 | | 10806 | 11243 | 11.5 × 3 = 34.5 |
| 27 | Patient Specimen C | 13153 | | |
| 28 | | 13036 | 13095 | 3.8 × 3 = 11.4 |

Quality Control Parameters:
TC = Total Counts;
NSB: Non-specific binding
MB = Maximum binding = 57.0%
% Intercepts: ED20: 136.2 ng/mL; ED50: 36.0 ng/mL; ED80: 9.60 ng/mL
Duplicate CPM column = CPM - NSB A. Manually-generated Standard Curve The standard curve is generated using peptide-N calibrators as follows:

1. The duplicate counts for non-specific binding (NSB) tubes are averaged.

2. The average cpm for the NSB tubes are subtracted from the cpm of maximum binding (MB), calibrators (A–E), controls, and patient sample tubes.

3. The percent maximum binding (% MB/TC) may be calculated for quality control.

4. The percent bound for each determination (B/MB×100) is calculated by dividing the corrected average counts for each determination by the maximum binding (MB) tube× 100.

5. The standard curve is generated by plotting CPM or %B/MB on the ordinate against the calibrator concentrations on the abscissa using semi-log paper.

6. The concentration of MPS-N for the unknown samples can be estimated by extrapolation.

7. Patient sample calculation: Multiply the result by the corresponding dilution factor. For example, 3× in the case of the standard dilution procedure (Table 4).

B. Computer-generated Standard Curves

Numerous computer programs may be use to calculate the results of the MPS-N test assay. The examples shown in FIGS. 2A, 2B and 2C were generated using one of such programs (Packard Instrument Co., Meriden Conn.). FIG. 2A shows a Semi-Log Point-to-Point plot; FIG. 2B shows a Four Parament Logistic plot; and FIG. 2C shows a Logit/

Log plot. After appropriate corrections, the program automatically connects the points between the mean of the calibrator duplicates. The values of the unknown samples are automatically extrapolated.

Acceptability of RIA Results

Assay runs are acceptable if the following criteria are met: test should only be performed by a qualified technologist or technician; values for duplicate determinations are within 13% of the mean CPM; the samples that have duplicate CPM values that differ from the mean CPM by more than 13% should be re-tested; the calibrators and control concentrations should fall within 13% of the value indicated in the vial; the laboratory temperature should be between 20–26° C.; each sample is run in duplicate as are all blanks, controls, and standards with no more than 20 unknowns per single run; if the result is greater than 100 ng/ml, the sample is re-run using a 1:1 and 1:10 dilution of patient serum; buffer D/Z is used as the diluent; the result by is multiplied by the dilution factor; the Gamma counter meets quality control requirements before being used to count tubes; and, all tubes are counted in a gamma counter for one minute with the window suitably adjusted for Iodine-125.

Quality Control

Good quality control includes the use of control samples within each assay to ensure that all protocols and reagents are performing correctly. The MPS-N assay contains all the necessary controls that can be used to validate the assay performance. The coefficient of variation for all calibrators and controls should be less than 13%. It is a worthy laboratory practice to record for each assay the dates, reconstitution of reagents, and QC parameters.

Sample handling: The instructions for handling and storage of biologic fluid samples should carefully be followed. Assay calibrators, controls, and patient samples should always be done in duplicate. Space duplicate control tubes throughout the assay to confirm the absence of any significant drift.

Controls: Controls (peptide N; 5 and 25 ng/ml) or serum pools with at least two MPS-N concentration levels (high and low) should be regularly assayed as unknowns. The results should be charted daily using Levey-Jennings plots for quality control.

Centrifugation: Centrifugation at 14,000×g for 20 min at 2–4° C. for sample preparation and at 3,000×g for 20 min at 10° C. for PEG precipitation should be strictly followed. A high-speed, refrigerated centrifuge is required.

QC Parameters: The inventor recommends the study of performance of the assay by using the following parameters:

TC: Total Counts (counts per minute; CPM)

% NSB (Non-Specific Binding)=100×(Average NSB Counts/Total Counts)

% MB (Maximum binding)=100×(Average MB Counts/Total Counts)

20, 50, and 80% intercepts. For example: 20%=peptide-N concentration at 20 percent bound; etc.

Performance Characteristics

The reliability of the MPS-N RIA procedure was evaluated by examining the reproducibility of measurements on selected samples that represent the range of values found in human sera, with particular reference to the low end of the RIA curve (10–30 ng/ml).

Intraassay Precision

Within run precision was determined by assaying samples containing various concentrations of MPS-N. Each sample was assayed 20 times in a single assay. The data and statistics are shown in Table 2 above and illustrated by FIG. 3.

Interassay Precision

Between run precision was determined by duplicate measurements of low and medium level patient samples in a series of 10 individual assays. The data and statistics are shown in Table 3, above and by FIG. 4.

Sensitivity

The detection limit of the assay, or minimal detectable dose is approximately 2 ng/ml.

Specificity

The antiserum is highly specific for the N-terminal domain of the human MPS-1 sequence. Peptide N completely neutralizes the binding of anti-peptide N antibodies to human recombinant MPS-1. With the exception of the immunoreactive MPS-N material in the human sera containing the N-terminal sequence of MPS-1 and the cellular MPS-1 proteins, the antiserum exhibits no significant cross-reactivity with other human cellular components.

Drift

Delays in additions of reagents may result in positional (or "end of-run") effects. The results of the measurement of the same samples in various positions show that there is no significant effect in assays involving 62 tubes or less. Thus, it is recommended that the samples are handled as sets of 60 when the PEG precipitating solution is added. This approach prevents any significant variation in the time of precipitation which may potentially lead to "end-of-run" effects. The data is shown below in Table 5.

TABLE 5

Drift
(Values represent ng/mL)

| Tubes | Sample 1 | Tubes | Sample 2 |
|---|---|---|---|
| 25–26 | 31.2 | 31–32 | 376.2 |
| 33–34 | 30.3 | 35–36 | 389.7 |
| 45–46 | 30.9 | 43–44 | 363.3 |
| 53–54 | 25.5 | 51–52 | 380.7 |
| 63–64 | 30 | 61–62 | 389.3 |

Parallelism

Figure 7:
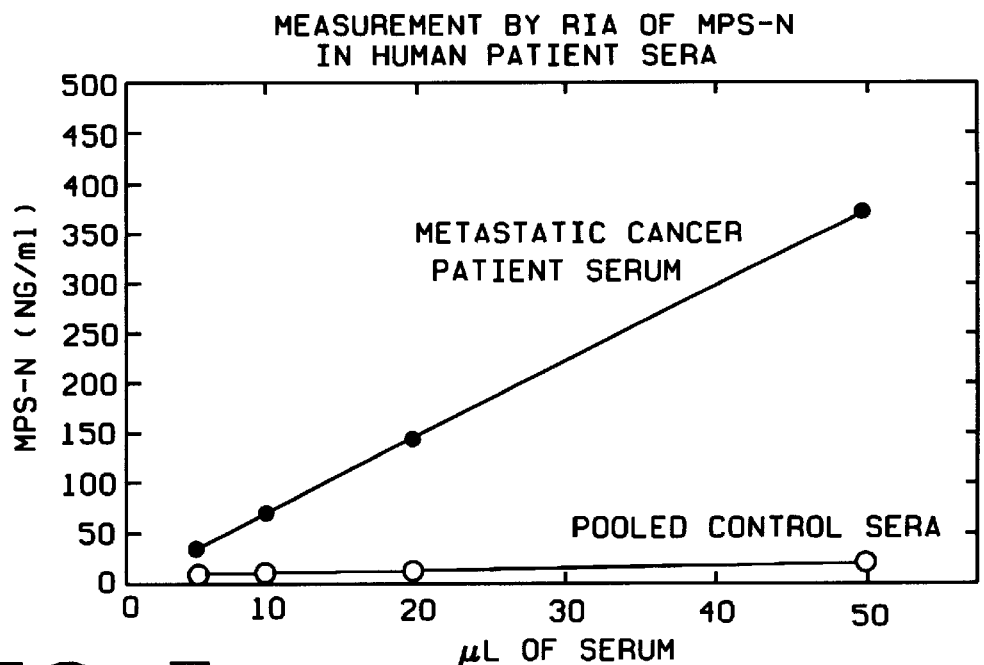
FIG. 7 is a graph illustrating the measurement of MPS-N in human sera by the radioimmunoassay method of the present invention.
Figure 8:
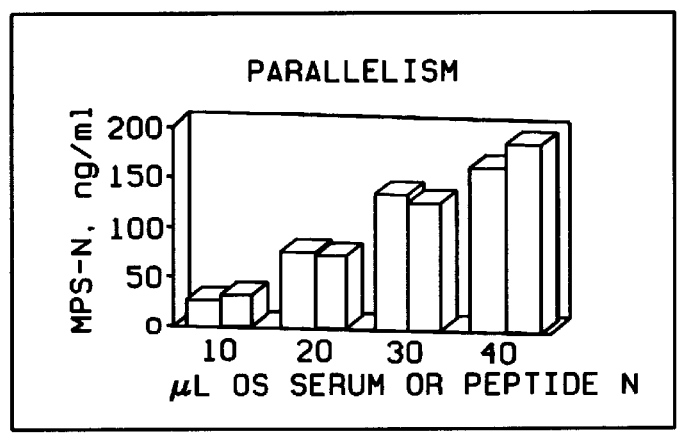
FIG. 8 is a graph illustrating parallelism.
Figure 9:
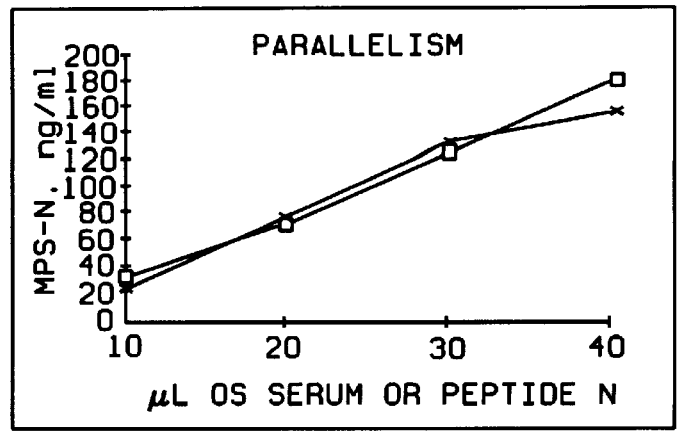
FIG. 9 is a graph illustrating parallelism.

Parallelism is defined as the extent to which the dose-response relationship between two materials (i.e., calibrator versus unknown specimens) is constant for the examined range of concentrations. To document parallelism, pooled control sera and cancer patient samples were assayed both undiluted and diluted with buffer D/Z. The example shown in FIG. 7 demonstrates that the RIA procedure maintains an excellent linearity under dilution with a variation that is within the precision of the assay. In addition, the data presented in Table 6 show both parallelism and the immunological identity of human serum MPS-N and peptide N. See also FIGS. 8 and 9.

TABLE 6

PARALLELISM AND IMMUNOLOGICAL IDENTITY

| Serum, uL | Serum, ng/mL | Peptide-N, ng/mL |
| --- | --- | --- |
| 10 | 25.5 | 31.7 |
| 20 | 76 | 73 |
| 30 | 137 | 131 |
| 40 | 167 | 190 |

These results also verify the absence of a significant protein-matrix effect: The peptide N-based calibrators are well matched to the supernatant matrix of the typical normal subject and cancer patient samples.

Protein Concentration

Figure 10:
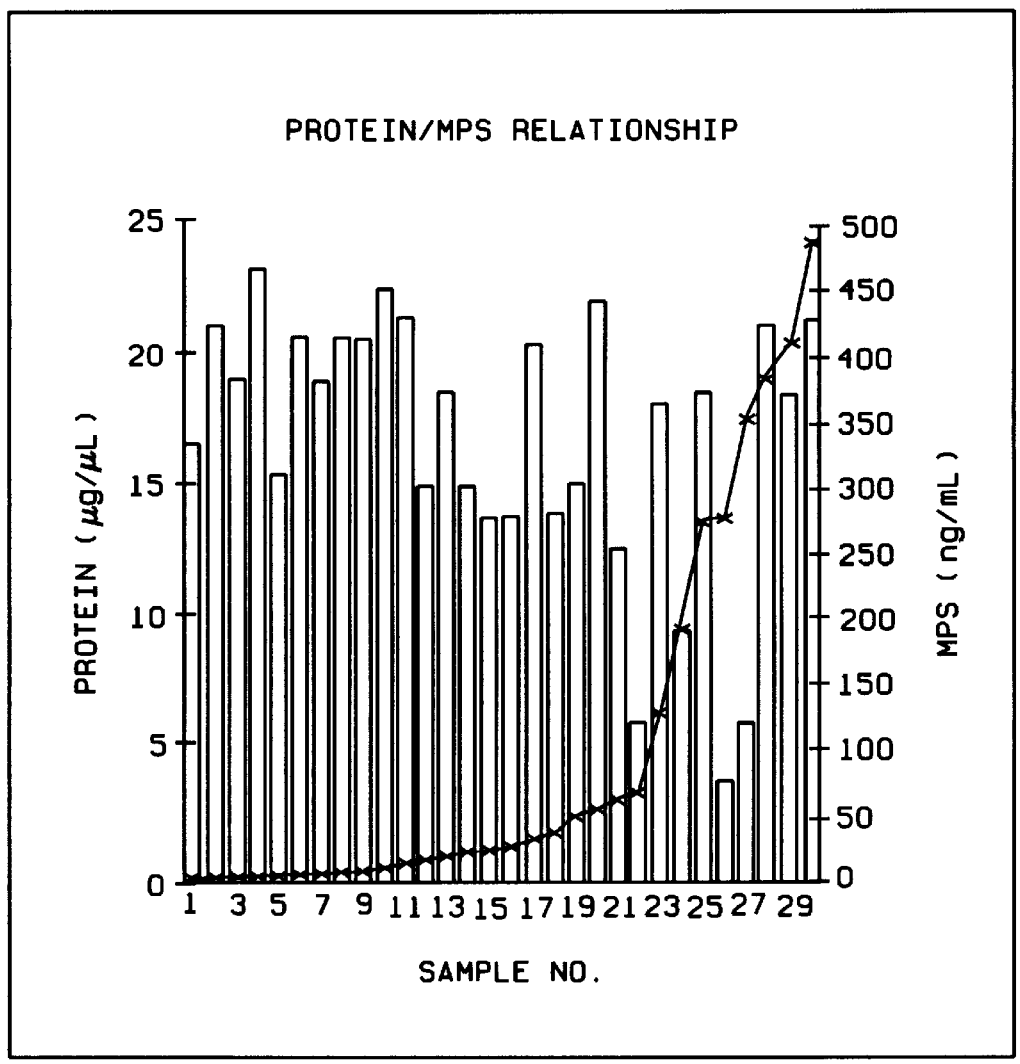
FIG. 10 is a graph illustrating the relationship between protein and MPS.
Figure 15:
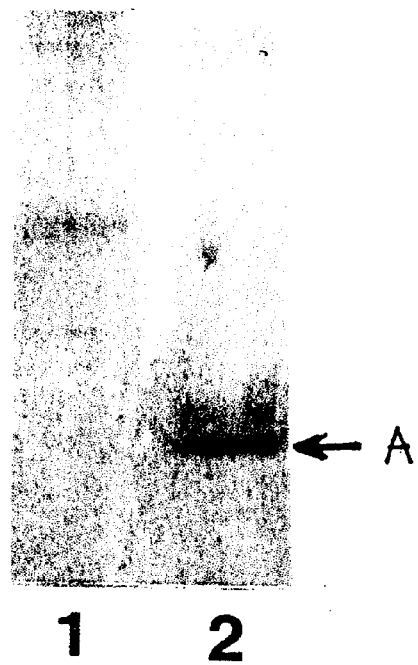
FIG. 15 is a Western blot analysis of heated human serum from a patient with metastatic prostate cancer using anti-MPS-N antibodies.

To determine if there is any effect of protein concentration in the MPS-N determinations, experiments were performed with the supernatants of patient samples which showed large variations in supernatant protein concentrations. The protein concentrations in the supernatants were measured in duplicate in 30 separate individual patient samples. In aliquots of the same samples, the MPS-N levels were determined in duplicate. The results, shown below in Table 7 as well as in FIG. 10, show that the concentrations of MPS-N do not correlate with protein concentrations in the supernatant. The results also indicate that the assay maintains good correlation with the clinical condition even in the presence of extreme variations in protein concentration which are frequently found in cancer patients.

TABLE 7

Protein/MPS Relationship

| Sample No | Protein ug/uL | MPS ng/mL |
| --- | --- | --- |
| 1 | 16.6 | 0.5 |
| 2 | 21 | 0.8 |
| 3 | 19 | 1 |
| 4 | 23.2 | 1.1 |
| 5 | 15.4 | 1.5 |
| 6 | 20.6 | 1.9 |
| 7 | 19 | 3.1 |
| 8 | 20.6 | 3.5 |
| 9 | 20.6 | 4.6 |
| 10 | 22.4 | 6.9 |
| 11 | 21.4 | 10.17 |
| 12 | 1.5 | 13.8 |
| 13 | 18.6 | 17.2 |
| 14 | 15 | 17.8 |
| 15 | 13.8 | 18.2 |
| 16 | 13.8 | 22.5 |
| 17 | 20.4 | 31.9 |
| 18 | 14 | 32.5 |
| 19 | 15.2 | 46.2 |
| 20 | 22 | 52.7 |
| 21 | 12.6 | 59.1 |
| 22 | 6 | 63.3 |
| 23 | 18.2 | 123.3 |
| 24 | 9.6 | 188.8 |
| 25 | 18.6 | 271.7 |
| 26 | 3.8 | 273.7 |
| 27 | 9 | 351.1 |
| 28 | 21.2 | 382.5 |
| 29 | 18.6 | 407.9 |
| 30 | 21.4 | 483.6 |

Recovery

Recovery was determined by measuring the increase in analyte concentration in a sample after adding a known amount of the analyte. For this purpose, various quantities of recombinant MPS-1 (R-MPS-1) or peptide-N were added to human sera containing endogenous MPS-N and the samples were assayed in duplicate. Three spiking solutions were prepared using the zero calibrator as diluent. The solutions (A, B and C) were made to represent 20 ng/ml of R-MPS-1, or 20 and 40 ng/ml Peptide N, respectively. To calculate expected values, the measured serum value was added to the measured R-MPS-1 or measured Peptide N values. Percent recovery is equal to the observed concentration of MPS-N divided by expected concentration of MPS-N times 100. The results shown in Table 8 below, demonstrate a recovery range of 94–99%.

TABLE 8

Recovery (values represent ng/mL)

| Sera Samples | R-MPS-1 Added | Peptide-N Added | Expected Concentration | Observed Concentration | %* Recovery |
| --- | --- | --- | --- | --- | --- |
| 2.4 | 21.8 | 0 | 24.2 | 23.9 | 99 |
| 15.2 | 19.4 | 0 | 34.6 | 34 | 98 |
| 10.5 | 0 | 19.1 | 29.6 | 27.7 | 94 |
| 10.5 | 0 | 39 | 49.5 | 48.2 | 97 |

*% Recovery: Observed concentration of MPS-N divided by expected concentration of MPS-N × 100.

Expected Values

MPS-N concentrations were determined in 632 individual samples. The relative distribution of MPS-N concentrations in healthy subjects, patients with various types of active cancer and patients with non-malignant diseases is presented in Table 1, above. The distribution for cancerous diseases consisted of active cases (clinical evidence of disease progression). In this study, 82% of the healthy subjects had MPS-N concentrations of 10 ng/ml or less.

Normal levels

Figure 11:
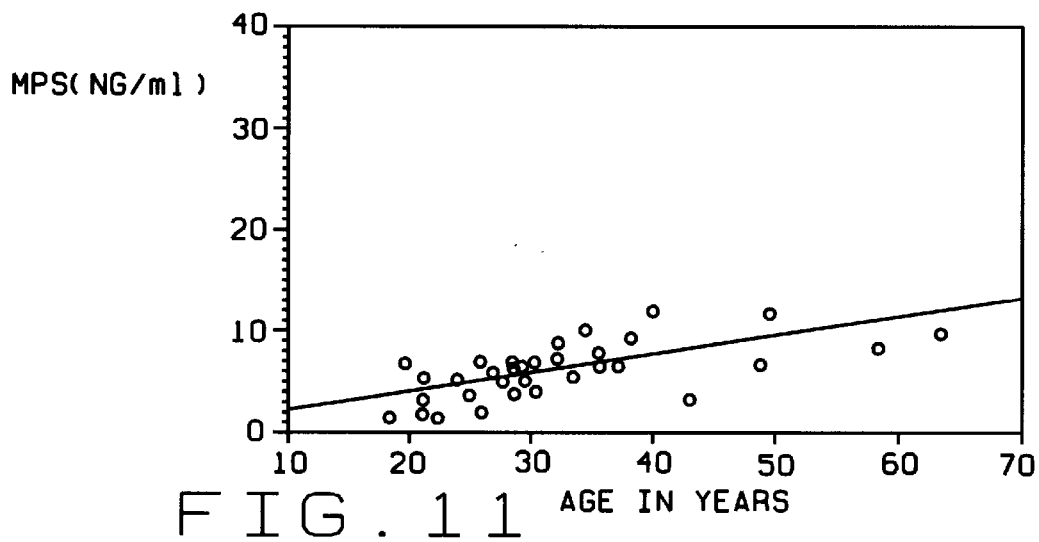
FIG. 11 is a graph illustrating adult normal MPS values as a function of patient age.
Figure 12:
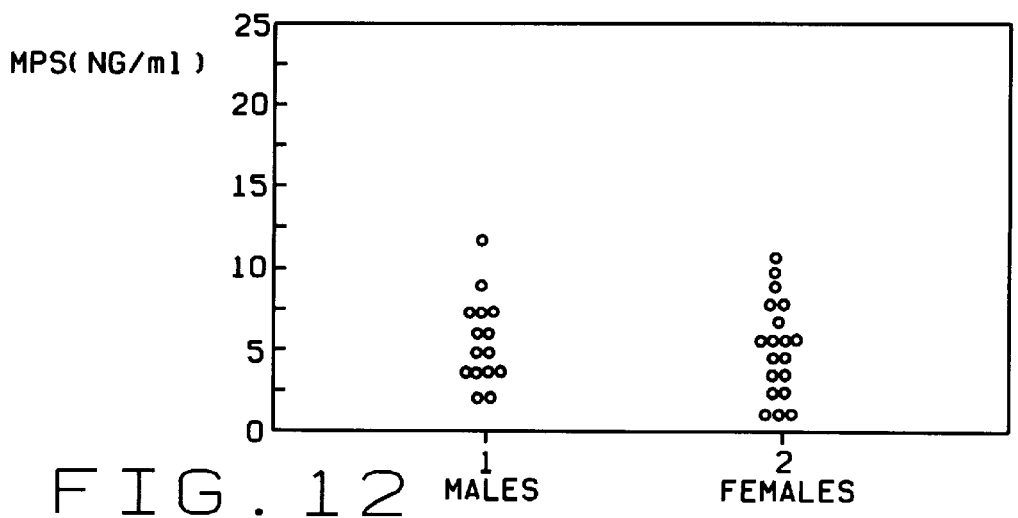
FIG. 12 illustrates the comparison of MPS values between men and women.

The results of studies with healthy subjects indicate a reference range for adults (19–88 years) of non-detectable to 10 ng/ml (82% of the healthy population). FIG. 11 shows that in healthy subjects the MPS-N Levels increase significantly with age, from approximately 4 ng/ml at age 20 years to about 10 ng/ml at age 50 years. FIG. 12 shows that there is no difference in MPS-N levels between male and female healthy subjects. Laboratories using the MPS-N test should consider these results a guideline only. Because the concentration of MPS-N is age related, and the possibility that different populations may have different base lines, it is necessary that each laboratory establish the normal range for a healthy population or for the population of interest.

If the assay value of a patient sample is between 10 and 20 ng/ml (17% of the presumed healthy subjects fall in this category; Table 1), it is recommended that a new MPS-N measurement is performed in 3 months.

Example of expected values in detection of Prostate Cancer

A retrospective clinical trial was conducted to test the effectiveness of MPS-N measurement to detect abnormal cell proliferation and/or active oncogenic processes related to prostate cancer. A total of 126 men 49 to 85 years of age were included in this study (Table 1). These studies demonstrated that the majority (97% or 122/126) of the active cancers were detected, when a cutoff value of 10 ng/ml MPS-N was used (Table 1). Further studies indicate that the levels of MPS-N correlate with the clinical stage of disease.

Thus, in patients suspected of having prostate cancer, MPS-N elevations greater than 10 ng/ml may indicate the existence of an abnormal proliferative and/or active oncogenic process that requires further clinical investigation by a physician.

Example of expected values for prognosis and management of prostate cancer

Figure 5:
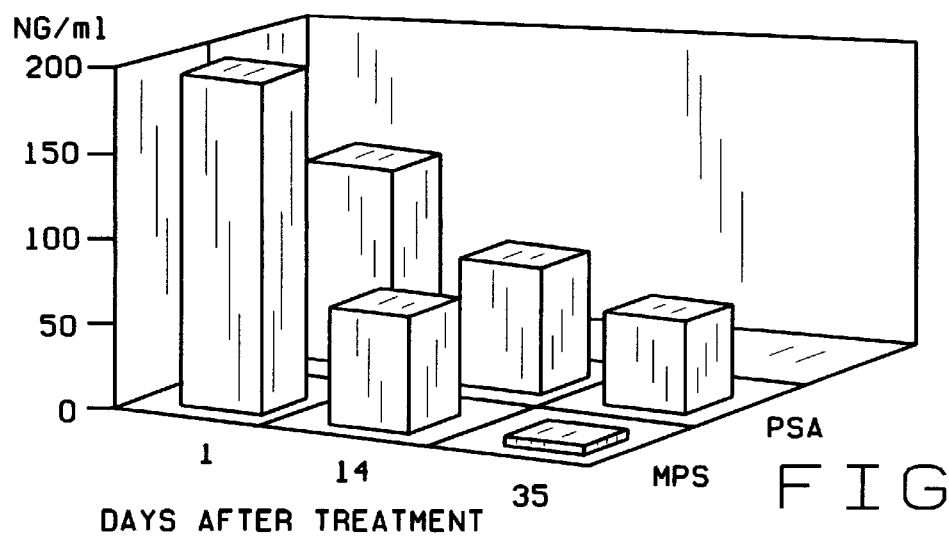
FIG. 5 is a graph illustrating post treatment decrease in serum MPS in a patient with prostate cancer.
Figure 6:
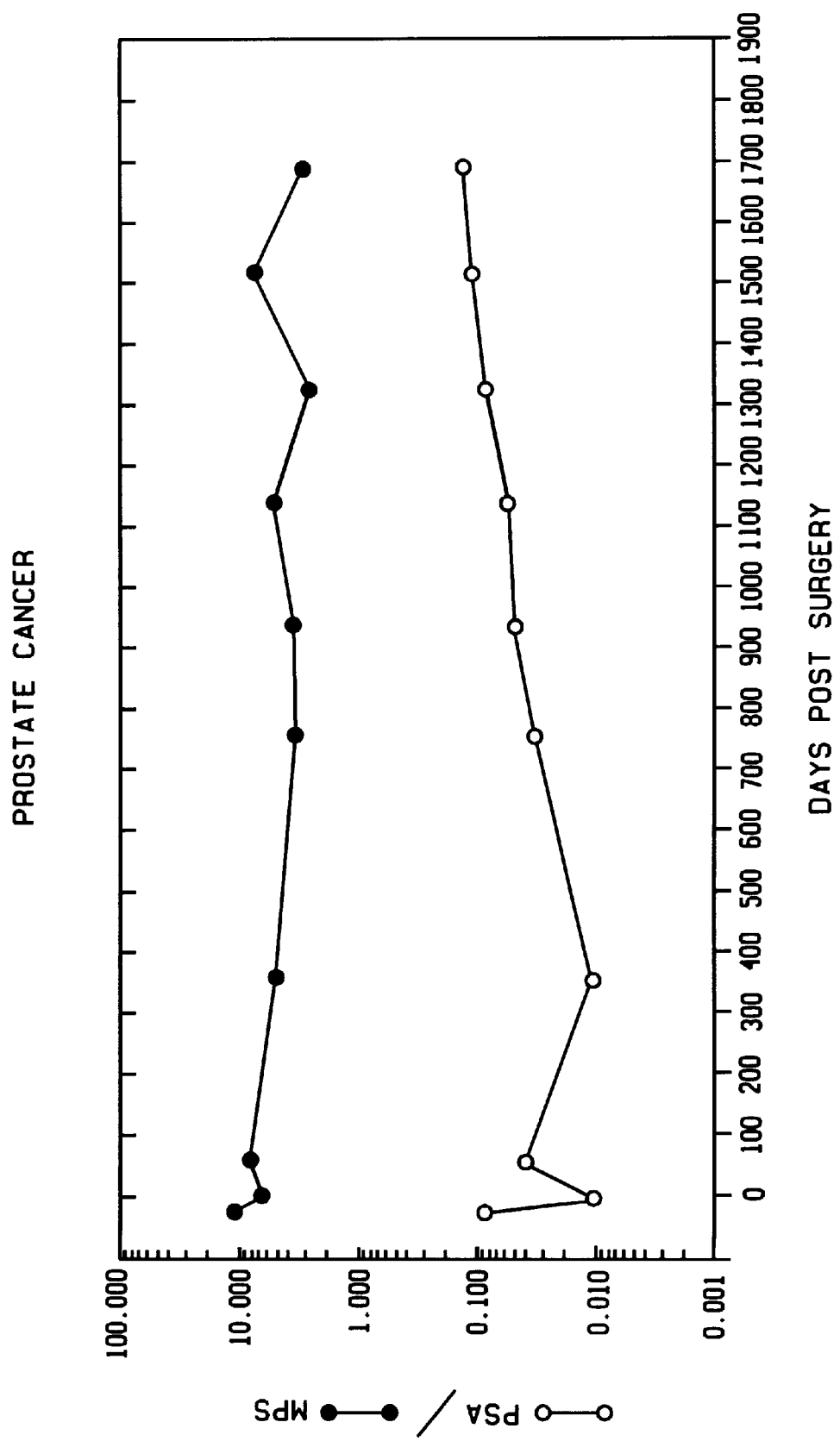
FIG. 6 is a graph comparing MPS and PSA values post-surgically in a patient with prostate cancer.

FIG. 5 illustrates the early decrease in MPS-N levels in a patient with prostate cancer which was treated with prostatectomy, chemotherapy and radiotherapy. The MPS-N levels decreased from 189 ng/ml (day 1), 73.8 ng/ml (day 14), to 8.7 ng/ml (day 35) after treatment, which correlated with clinical evidence of successful therapy. Moreover, long-term follow up studies demonstrated that three patients free from prostate cancer disease for approximately 4 years after treatment showed MPS-N levels consistently lower than 10 ng/ml in serial determinations for approximately 4 years after treatment. An example of one of such cases with a follow up of 4.6 years after treatment is shown in FIG. 6.

False Positive and False Negative Results in Various Pathological Conditions

As with any other medical test that determines the concentration of proteins in the human serum, severe/extreme cases of organ failure such as liver, kidneys, massive brain damage, massive muscle damage, septicemia and in terminal patients, the test can show falsely positive or negative results. For example, renal insufficiency may impair the normal excretion mode of MPS-N and lead to false-positive results. In addition, iatrogenic influences such as colonoscopy, cystoscopy, etc, may lead to the release of MPS-N protein from the cells into the circulation. Iatrogenic medications may also cause alterations in the release of MPS-N protein into the circulation.

False Positive Results During Pregnancy

Because the MPS-N protein is produced by the embryo and it is also produced and released by the trophoblastic cells of the developing placenta, the MPS-N protein is present in the sera of pregnant women. Thus, the MPS-N test cannot be used in pregnant women.

Interfering Substances

In vitro interferences can by caused by EDTA, citrate and heparin. In vivo interferences can be caused by extremely high concentrations of hemoglobin, bilirubin or triglycerides.

Alternative Embodiments

Alternative embodiments of the assay of the present invention are illustrated generally in FIGS. 15–20. The embodiments of FIGS. 15–20 involve a universal method of detecting neoplasms including benign and malignant tumors, generally by isotopic or non-isotopic measurements of proteins common to various forms of cancer. The general principle of this embodiment is that specific proteins present in the body fluids of cancer patients, after heating the body fluid to activate or release the specific proteins, are capable of inhibiting the binding and/or precipitation of a first antibody by a second antibody.

A systematic analysis of heated plasma samples by Western blot analysis shows the presence of a differential pattern of proteins in normal subjects in comparison to cancer patients. The samples were heated in accordance with the description above and in accordance with the procedures disclosed in co-pending application Ser. No. 08/581,072, now U.S. Pat. No. 5,668,016. A Western blot analysis of serum from a patient with metastatic prostate cancer using anti-MPS-N antibodies is provided in FIG. 15 and shows the presence of a differential pattern of proteins in comparison to normal patient serum (not shown) shown to have sequence homology with MPS-1 proteins, as described above. After electrophoresis and transfer of two aliquots of heated cancer patient serum, Western blot analysis was performed with anti-MPS-N antibodies. Lane 1: anti-MPS-N antibodies were neutralized with the N-peptide. It will be noted that no bands are observed, showing specificity of anti-MPS-N antibodies for the N-terminus portion of MPS-1. Lane 2: anti-MPS-N antibodies alone react strongly with band A, present in the serum of patients with cancer. The results of sequencing showed that band A is identical to C3a of complement (anaphylatoxin), which has a sequence homology to the N-terminus of human MPS-1. However, it will be apparent to those skilled in the art that the embodiment of present invention can be used to detect proteins having sequence homology to MPS-1, MPS-N, MPS-1-like proteins, MPS-N-like proteins and to other proteins unrelated to MPS, as will be explained in detail below.

It was determined upon further research that some of the protein bands interact with anti-MPS-N antibodies. Sequence analysis of those bands indicated that one of the bands that reacted with anti-MPS-N antibodies. Sequence analysis of the bands that reacted with anti-MPS-1 antibodies was C3a segment of complement (anaphylatoxin) of molecular weight 9,100. This band has a sequence similarity with MPS-1 at the N-terminal portion that clearly shows cross reactivity with the anti-MPS-N antibodies. Other bands did not react with anti-MPS-N antibodies such as haptoglobin, and a newly identified high molecular weight 200 kDal protein were also present in high concentration in serum of cancer patients. Additional fragments of complement were also identified in the heated samples.

In one specific embodiment of a cancer detection test, anaphylatoxin measurement can be used to detect cancer. Since C3a (e.g. anaphylatoxin) is present in direct proportion to the presence of cancer, measurement of anaphylatoxin by direct immunoassay in heated serum from patients with cancer, using the procedure described above with reference to detecting MPS-like proteins, is used to detect cancer. Furthermore, the antibodies 1 and 2 described in the first embodiment can be anti-MPS-N antibodies (due to the amino acid sequence homology between MPS-N and anaphylatoxin) or antibodies 1 and 2 employed in the procedure can be anti-anaphylatoxin antibodies.

The specific test procedures are the same as those described above with regard to the radioimmunoassay of MPS proteins with anti-anaphylatoxin (C3a) antibodies used instead of MPS-N antibodies. Thus, the previously described methods and materials are incorporated into the description of this embodiment by reference, with the understanding that anti-anaphylatoxin antibodies are substituted for MPS-N antibodies.

Another test method of the present invention is based on inhibition of a reaction of a second antibody with a first antibody. The test method more specifically is based upon the inhibition or interference with the binding and/or precipitation of a first antibody by a second antibody. Generally speaking, the proteins that are detected are elevated in the serum of a subject having cancer and because they bind to the first antibody in the non-antigen binding site (Fc portion, complement binding site) they inhibit the binding and/or precipitation of a first antibody by a second antibody. The inhibition of binding and/or precipitation can be detected and, hence, the presence of the elevated protein is detected. This novel method represents a non-classical immunoassay. These proteins may be MPS-N related, such as anaphylatoxin or unrelated to MPS-N such as other components of the complement are any other interfering proteins elevated in the serum of cancer patients.

Figure 16:
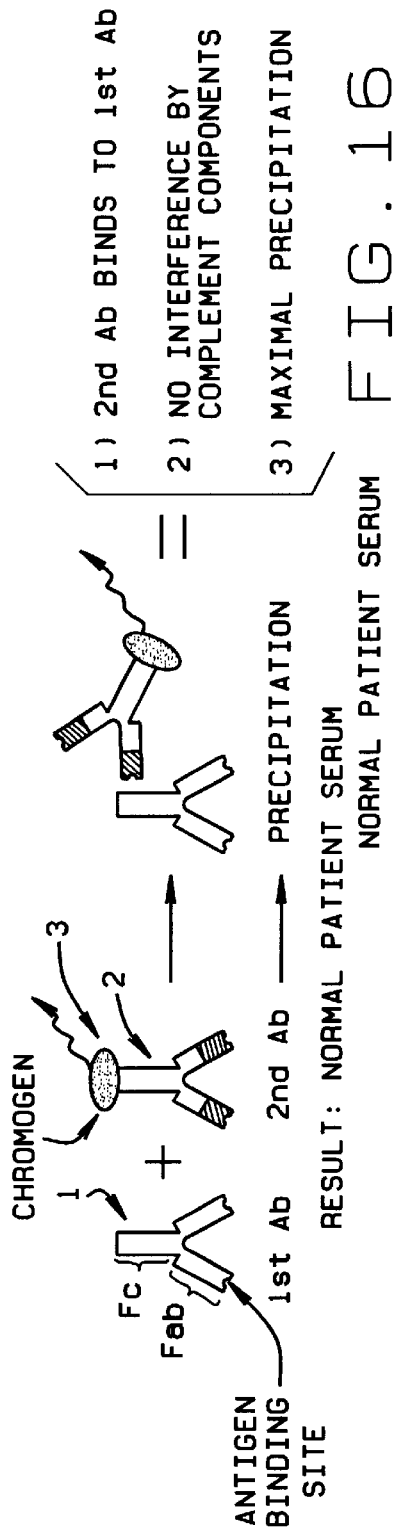
FIG. 16 is a schematic representation of one method of the present invention applied to normal sera.
Figure 17:
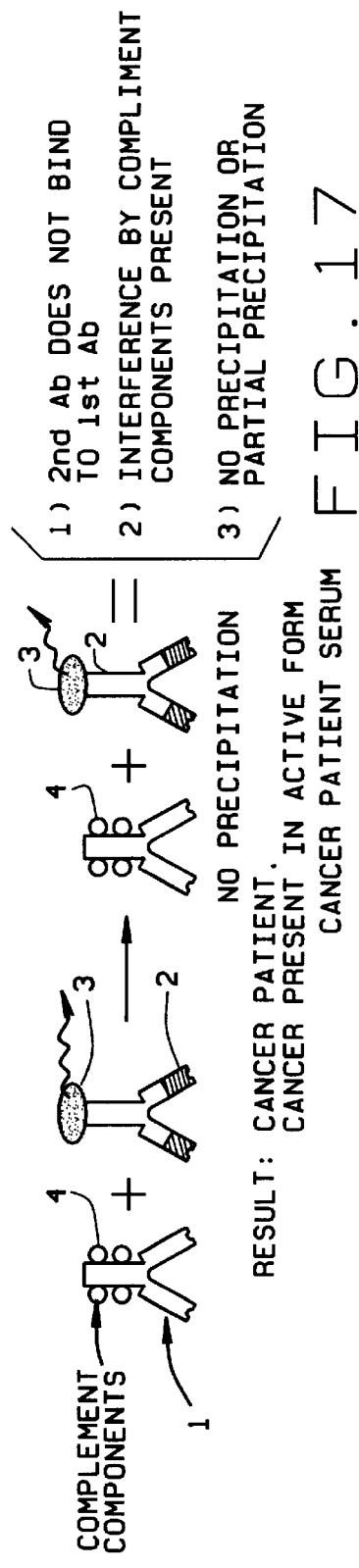
FIG. 17 is a schematic representation of the method of FIG. 16 applied to sera of a cancer patient.

The principle of the procedures of this alternative embodiment of the present invention are illustrate in FIGS. 16 and 17. FIG. 16 is a schematic illustration of the application of the present principles to normal serum, that is, serum of a patient not having cancer. The serum was prepared according to the principles outlined above by heating in a diluent devoid of magnesium and calcium for 1 to 10 minutes, preferably 3 minutes, at 100° C. A first antibody 1 is added to the serum. A second labeled antibody 2 is then added to the serum. The second antibody is labeled with a marker such as chromogen agent 3, which can be fluorecently labeled, enzymatically labeled, radioactively labeled, bioatinylated or any other acceptable label, now know or unknown. As show in the schematic, the second antibody 2 binds to a binding site, e.g. the Fc portion or complement binding site for maximum precipitation of the first antibody 1 with the second antibody 2. The amount of precipitation can be measured by measuring the labeled precipitate or visualizing the marker.

FIG. 17 indicates, schematically, the method of the present invention as applied to serum of a cancer patient. As can be appreciated, the serum is prepared as stated above. The first antibody 1 is added to the sera. An interfering substance, such as complement components 4 attaches to the complement binding site. The second labeled antibody is added to the sera. As can be seen and appreciated, since the binding site is occupied by the complement 4, second antibody 2 cannot bind to antibody 1 and, hence, cannot precipitate the first antibody 1. Therefore, there is no antibody 1-labeled antibody 2 precipitate to measure by acceptable methods. Thus, the absence of labeled precipitate indicates and increased level of complement 4. The procedure can use any antibody which can bind complement and any antibody which can bind to the first antibody.

The cancer detection test thus involves the measurement of inhibition of precipitation by complement-related proteins. This is a non-classical or novel immunoassay which measures heat-resistant complement-related proteins in plasma or other fluids of individuals with various human tumors. It is known that cancer cells produce complement and that complement is elevated in the presence of cancer, in linear proportions. Thus, increased levels of complement components can be detected due to (1) direct production of complement by cancer cells, or (2) exogenous complement, that is, complement produced by non-cancer cells involved in tumor destruction, which is activated to attack cancer cells. Therefore, since complement-related proteins are expressed by neoplasias or in response to neoplasias, and are present in the plasma, measurement of inhibition of precipitation by radioimmunoassy or any other method of detecting the presence or absence of precipitation in heated serum sample from patients with cancer can be used to detect cancer.

Figure 18:
FIG. 18 is an schematic representation of anaphylatoxin formation.

The importance of the heating or serum preparation and activation in accordance with the principles of co-pending application Ser. No. 08/581,072, now U.S. Pat. No. 5,668, 016 will be appreciated by those skilled in the art. As stated above relative to the test for MPS proteins, the novel heating step allows for the partial denaturization of the proteins resulting in a relative enhanced availability of the target proteins. With regard to the testing for complement and/or segments thereof, the novel heating step is similarly important both in the direct measurement of anaphylatoxin using the procedures similar to the test for MPS proteins, or when determining the inhibition of precipitation. For example, complement C3, as shown in FIG. 18, has an N-terminal segment designated as C3a. Cleavage of C3 by convertase liberates the anaphylatoxin (C3a) from the NH2 terminus of the alpha chain but generates C3b. C3 and C3a has a sequence homology to MPS proteins. Moreover, the inventor has determined that the novel heating step partially denatures the C3 protein, cleaving the C3a segment and making it available for detecting in a sample, either by direct measurement by RIA as described above with reference to anaphylatoxin, or by the inhibition of precipitation by complement components. This partial denaturing is a result of heat-related cleavage of the C3a portion, either by direct heat-dependent denaturization or by the heat induction of convertase activity or both, and is important to the detection of the presence of C3a because there are competing types of complement or other types of complement elevated in other disease states that do not include the C3a (or homologous segments). By partially denaturing the resulting C3a, which has been shown by Western blot to be present and thus heat resistant, can be measured. C3a is believed to be present as one segment of complement detected in cancerous states when the method of heating the sample is used.

Figure 19:
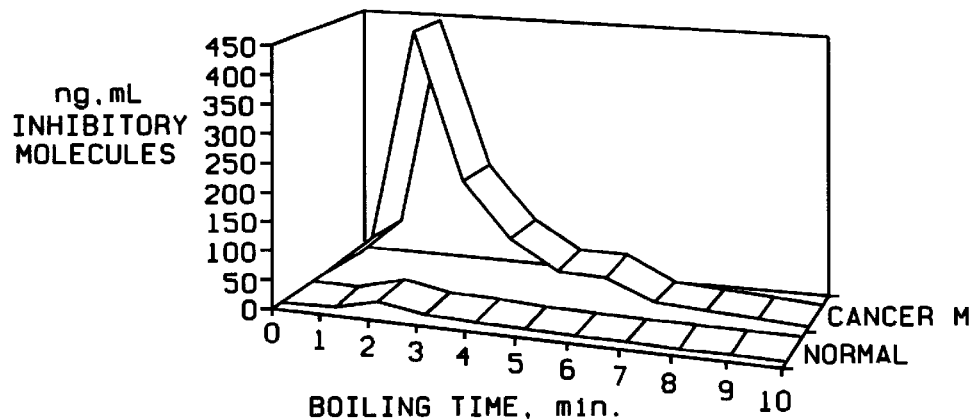
FIG. 19 is a graph illustrating the inhibition of precipitation detected by fluorescent second antibody.

FIG. 19 graphically illustrates the relationship of heating the serum sample to the detection of inhibition of precipitation detected by fluorecently labeled second antibody. It is clear from FIG. 19 that the subjecting the sample to 100° C. (boiling) for 1 to 5 minutes, preferably 2 to 4 minutes and most preferably for 3 minutes yields the best results.

Figure 20:
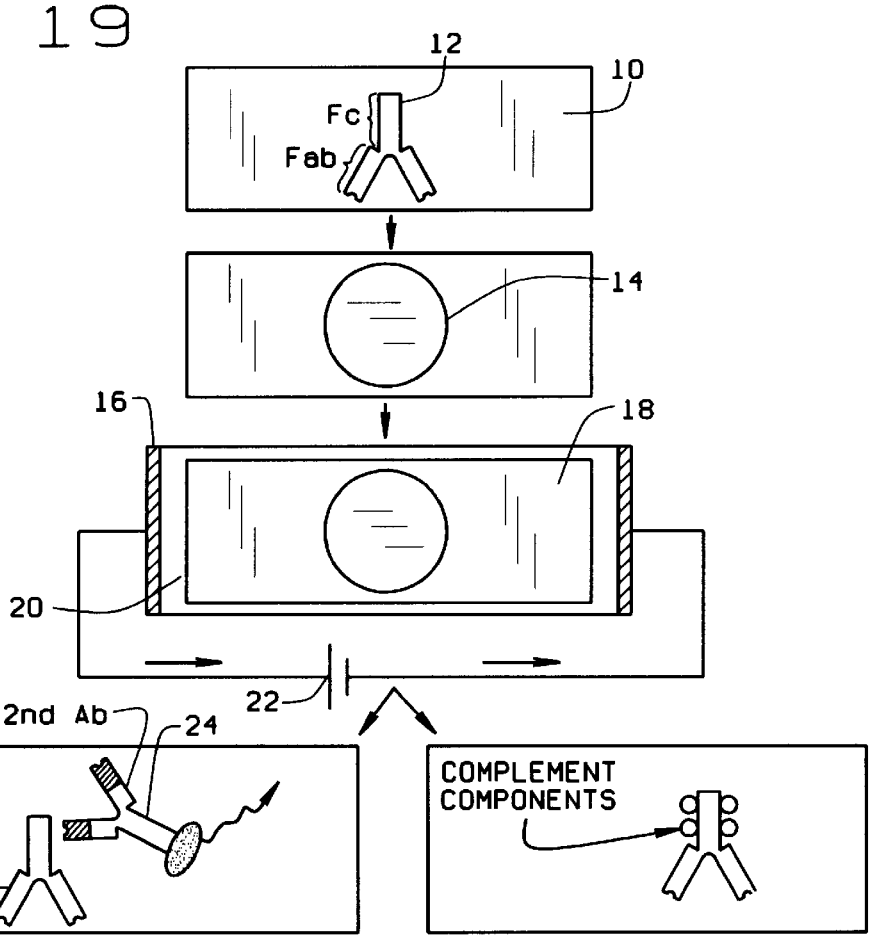
FIG. 20 is a schematic representation of a test and apparatus of the present invention.

FIG. 20 illustrates one embodiment of a rapid test for the detection of the presence of a protein capable of interfering with a reaction between a second antibody and a first antibody, for example a protein capable of interfering with the binding of a first antibody by a second antibody of the precipitation of a first antibody by a second antibody. It will be appreciated that the test, as described, can be provided as a portable, easy-to-use, self administered test to determine the presence of such proteins elevated in the blood of patients with cancer. The test includes a substrate 10 such as filter paper or other appropriate substrate. The substrate has a first antibody 12 thereon, preferably covalently bonded to the substrate in a conventional manner. A serum sample 14, such as a drop of blood is added to the antibody 12 and allowed to dry. The substrate is then heated. In one embodiment, a heating apparatus 16 is provided. Heating apparatus 16 includes a chamber 18 including a high resistance buffer 20. An energy source, for example a battery 22 provides electrical flow through the resistant buffer 20 to generate heat. Preferably, the temperature is raised to 100° C. for approximately 3 minutes. The heat activates the target proteins in the sample in accordance with the principles described above. After heating, the substrate 10 is washed, for example with deionized water, and a second antibody 24 is introduced to the serum sample and first antibody. The substrate then is incubated for 5 minutes to one hour, preferably 15 minutes to an hour, most preferably about 15 to 30 minutes at room temperature. The substrate is again washed. A chromogen, for example BCIP or any other coloring or chromogenic agent having an affinity for the second antibody is added to detect the second antibody. If the reaction between the first antibody 12 and the second antibody is interfered with by a protein, as at 26, such as a complement product that blocks the second antibody binding site, and prevents the second antibody from binding with the first, the second antibody, with it chromogen marker will be removed by the second wash step. An absence of detectable marker on the substrate indicates a high level of interfering protein in the serum, thus indicating cancer. In the absence of an interfering protein, second antibody 24 will bind to the first antibody 12 and not be removed by washing. The chromogen or marker can be viewed. Hence, the test indicates no cancer. It will be evident that variations of the described test and apparatus can be derived that incorporate the novel concept of detecting the presence of proteins elevated in cancer that interfere with the binding or precipitation of a first antibody by a second antibody all of which are intended to fall within the scope of the appended claims.

It should be appreciated that the novel method of detection of cancer through the detection of inhibition of binding or precipitation of a first antibody by a second antibody is not limited to antibodies against MPS-N, anaphylatoxin or the C3a segment of anaphylatoxin. The method can be applied to detect the presence of any other protein, for example other complement components or combinations thereof or similar or even disparate substances that are elevated in the presence of cancer or any other disease state, so long as a first antibody with an affinity for the protein and a second labeled antibody with an affinity for the first antibody can be produced. Thus the scope of the instant invention is intended not only to include tests for known proteins with known antibodies, as disclosed, but also tests for proteins yet unknown with antibodies yet unknown where the target protein competes with or interferes with the precipitation or binding of a first antibody by a second antibody.

It will be understood from the foregoing discussion that various changes and modifications may be made in the method and the kit of the present invention without departing from the scope of the appended claims. For example, the test can be used to determine the presence of target proteins in biologic fluids other than sera. Also for example, any of the optional materials could be included in the kit, along with the materials that are essential to the working of the method of the present invention. Therefore, the foregoing description, tables and accompanying drawings should be viewed as illustrative only and not in a limiting sense.

I claim:

1. A method for detecting the presence of a target protein which binds to the Fc portion of a first antibody and which is elevated in the serum of a subject with a neoplasm comprising
   a) heating a serum sample;
   b) adding a first antibody to the heated serum sample
   c) adding a second antibody, which binds specifically to the Fc region of said first antibody, to said serum sample;
   d) detecting the blocking of binding of said second antibody to said first antibody by absence of precipitation of said first antibody;
   wherein said absence of precipitation of said first antibody detects the presence of said target protein.

2. The method of claim 1 wherein the second antibody is labeled with a marker so as to enhance the detection of binding of the second antibody with the first antibody.

* * * * *